(12) United States Patent
Itomi

(10) Patent No.: US 7,151,383 B2
(45) Date of Patent: Dec. 19, 2006

(54) OIL CONDITION SENSOR

(75) Inventor: Shoji Itomi, Kuwana (JP)

(73) Assignee: NTN Corporation, Osaka (JP)

( * ) Notice: Subject to any disclaimer, the term of this patent is extended or adjusted under 35 U.S.C. 154(b) by 0 days.

(21) Appl. No.: 11/087,753

(22) Filed: Mar. 24, 2005

(65) Prior Publication Data

US 2005/0212533 A1   Sep. 29, 2005

(30) Foreign Application Priority Data

Mar. 26, 2004   (JP) .............................. 2004-091029

(51) Int. Cl.
*G01R 27/08* (2006.01)
*G01N 33/20* (2006.01)

(52) U.S. Cl. ...................... 324/698; 324/724; 73/61.42

(58) Field of Classification Search ................ 324/553, 324/698, 693, 691, 649, 600, 439, 446, 705, 324/722, 696, 724, 204, 219, 228, 71.1; 73/53.05, 73/53.06, 53.07, 61.42, 61.71
See application file for complete search history.

(56) References Cited

U.S. PATENT DOCUMENTS

| | | | | |
|---|---|---|---|---|
| 4,323,843 A | * | 4/1982 | Batham | 324/204 |
| 5,262,732 A | * | 11/1993 | Dickert et al. | 324/672 |
| 5,457,396 A | * | 10/1995 | Mori et al. | 324/724 |
| 5,614,830 A | * | 3/1997 | Dickert et al. | 324/553 |
| 6,377,052 B1 | * | 4/2002 | McGinnis et al. | 324/446 |
| 6,556,026 B1 | * | 4/2003 | Ogimoto et al. | 324/698 |
| 6,803,775 B1 | * | 10/2004 | Sanchez et al. | 324/698 |

FOREIGN PATENT DOCUMENTS

JP   2002-286697   10/2002

* cited by examiner

*Primary Examiner*—Vincent Q. Nguyen
*Assistant Examiner*—Hoai-An D. Nguyen
(74) *Attorney, Agent, or Firm*—Wenderoth, Lind & Ponack, L.L.P.

(57) ABSTRACT

An oil condition sensor is proposed which can accurately determine the degree to which oil is contaminated with metallic powder. It includes a permanent magnet and a sensor head provided around the permanent magnet. The sensor head includes a cup-shaped electrode and a plurality of rod-shaped conductors that are axially spaced from the cup-shaped electrode. The conductors are connected to a power supply through separate resistors. When the amount of metallic powder in the oil increases, a greater number of conductors are electrically connected to the cup-shaped electrode. Thus, by finding the number of conductors electrically connected to the cup-shaped electrode, it is possible to determine the degree to which the oil is contaminated with metallic powder. Since the resistors need not be immersed in the oil, their specific resistivities will scarcely change, so that the degree of contamination of the oil can be determined with high accuracy.

6 Claims, 5 Drawing Sheets

OIL CONDITION SENSOR

BACKGROUND OF THE INVENTION

The present invention relates to an oil condition sensor used to check the degree of contamination of automotive transmission oil or engine oil.

Such an oil condition sensor is mounted in an oil container for automotive transmission oil or engine oil and is used to check how the oil is contaminated with iron powder or other metallic powder that are produced when automotive parts are abraded against each other. A typical such sensor is disclosed in JP patent publication 2002-286697 (see especially its FIGS. 1–4). It includes a rod adapted to be immersed in oil. The rod carries magnets at its tip. A pair of electrodes are provided around the magnets, axially spaced from and opposed to each other. The sensor produces a signal corresponding to the resistance in the oil between the electrodes, which in turn corresponds to the amount of metallic powder in the oil.

At least one of the electrodes is a resistor. Any conductive material in the oil such as iron powder tends to be magnetically attracted toward the outer peripheries of the magnets and stuck on an end face of the resistor. The resistance between the electrodes is a function of the area of a conductive material covering the end face of the resistor. Specifically, the resistance $\Omega$ between the electrodes is given by $R_0 \times (100/S)$, where $R_0$ is the specific resistance of the resistor, and S is the percentage of the area of the conductive material covering the end face of the resistor. From this equation, one can see that the higher the value S, i.e. the degree of contamination of the oil, the smaller the resistance between the electrodes. The resistor forming one of the electrodes may be made of a conductive resin containing carbon, a good conductor, or a conductive ceramic material. According to this publication, instead of using a resistor for at least one of the electrodes, a resistive material may be applied to the outer surface of a tubular insulating cover that is disposed between magnets and the electrodes.

As explained above, the resistor or the resistive material is an essential element for the oil condition sensor of this publication. Such a resistor or resistive material tends to be internally stressed when the load and/or temperature changes. Such internal stresses in turn cause fluctuations in the specific resistance $R_0$ of the resistor or resistive material. Because the specific resistance $R_0$ easily fluctuates, it is impossible to stably and reliably detect the resistance between the electrodes, so that no accurate determination of the degree of contamination of oil is possible.

An object of the invention is to provide an oil condition sensor which can accurately determine the degree to which oil is contaminated with metallic powder.

SUMMARY OF THE INVENTION

According to the present invention, there is provided an oil condition sensor comprising a rod having a tip portion adapted to be immersed in oil, a magnet mounted around the tip portion, a pair of electrodes mounted around the magnet so as to be axially spaced from each other, one of the pair of electrodes comprising a plurality of conductors, the conductors being electrically connectable to the other of the pair of electrodes through any metallic powder present in the oil, whereby the amount of metallic powder in the oil is inferable from the number of conductors that are electrically connected to the other of the pair of electrodes.

With this arrangement, it is possible to accurately determine the degree to which the oil is contaminated with metallic powder.

The conductors may be connected to a power supply through separate fixed resistors. With this arrangement, by measuring the partial voltage of the sensor head assembly, it is possible to detect the number of conductors that are electrically connected to the other of the pair of electrodes.

Alternatively, the conductors may be connected to a power supply through separate elements that react to electricity passed therethrough. With this arrangement, by counting the number of elements that have reacted to electricity, it is possible to determine the number of conductors that are electrically connected to the other of the pair of electrodes. The elements that react to electricity may be small light bulbs or LED's.

Preferably, each of the conductors is spaced from the other of the pair of electrodes by a distance that is different from any of the distances between the other of the conductors and the other of the pair of electrodes. With this arrangement, when the oil becomes increasingly contaminated, the conductors will be electrically connected to the other of the pair of electrodes one after another with those closer to the other of the pair of electrodes being connected earlier. Thus, it is possible to accurately determine the degree to which the oil is contaminated with metallic powder from the number of conductors that are electrically connected to the other of the pair of electrodes.

BRIEF DESCRIPTION OF THE DRAWINGS

Other features and objects of the present invention will become apparent from the following description made with reference to the accompanying drawings, in which.

DETAILED DESCRIPTION OF THE PREFERRED EMBODIMENTS

Figure 1:
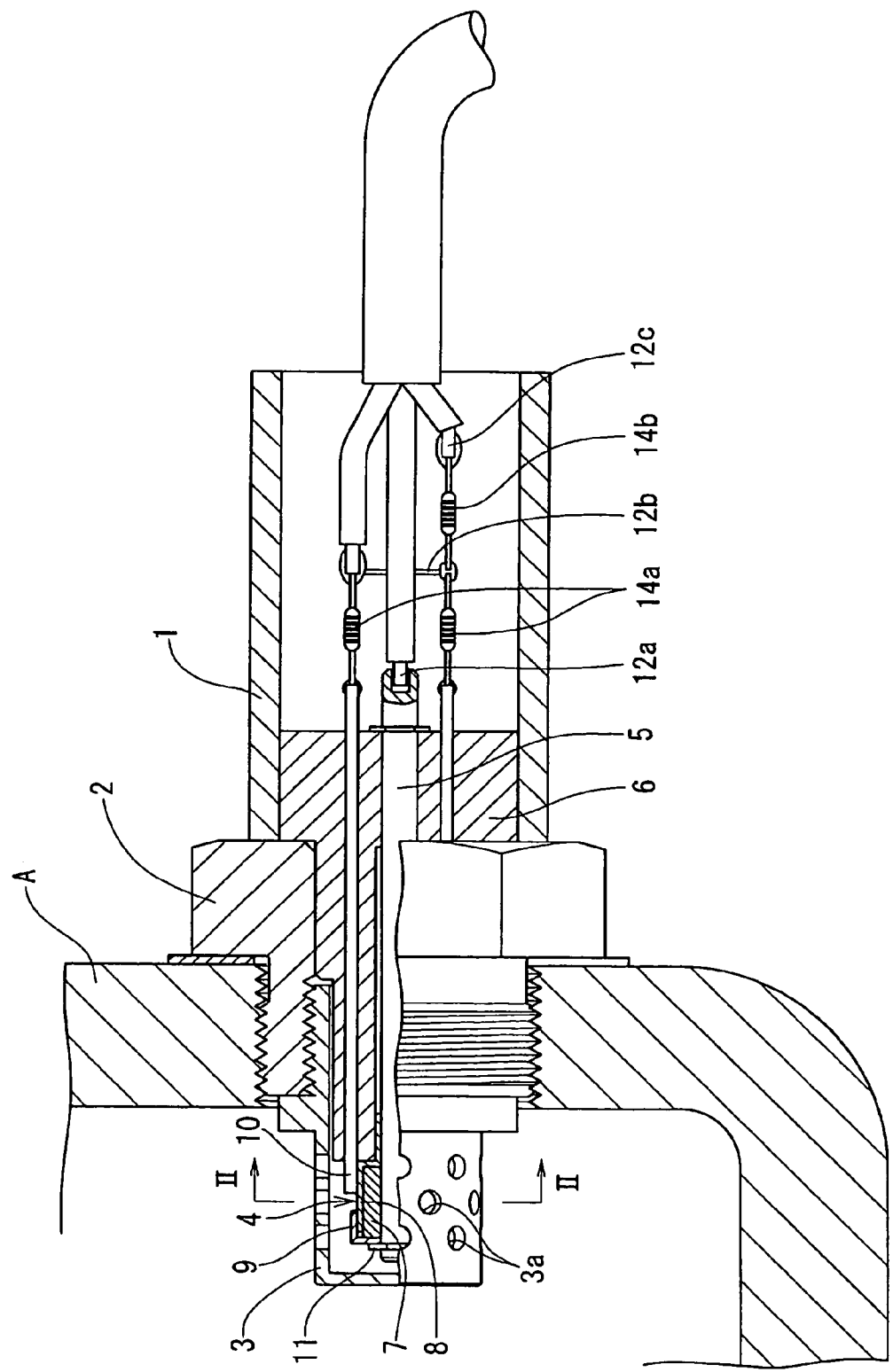
FIG. 1 is a partial vertical sectional view of an oil condition sensor of a first embodiment according to the present invention.

Now the embodiments of the invention are described with reference to the drawings. FIGS. 1–4 show the oil condition sensor of the first embodiment. It is used to determine the degree to which automotive transmission oil is contaminated with metallic powder, and includes, as shown in FIG. 1, a nut 2 threaded into a lower portion of a side wall of an oil pan A for transmission oil, a casing 1 fixed to the nut 2 outside the oil pan A, and a head cover 3 threaded into the nut 2 inside of the oil pan A so as to be immersed in the oil. A sensor head assembly 4 is mounted in the head cover 3. The head cover 3 is formed with a plurality of holes 3a through which oil in the oil pan A can flow into the head cover 3.

A rod 5 made of a conductive material extends through the casing 1 and is held in position so as to be coaxial with the casing 1 by a holder 6 received in the casing 1. A ring-shaped permanent magnet 7 is fitted around the tip of the rod 5 protruding from the holder 6 into the casing 1. A tubular insulating cover 8 is provided around the permanent magnet 7. A cup-shaped first electrode 9 is fitted on the rod 5 so as to surround the insulating cover 8. A plurality of (eight in the embodiment shown) rod-shaped conductors 10 as a second electrode extend through the holder 6 with their end portions protruding therefrom into the head cover 3 so as to be axially spaced from the rear end (right-hand end in FIG. 1) of the first electrode 9 around the rod 5. The sensor head assembly 4 comprises all of the elements present in the space defined in the head cover 3.

Figure 2:
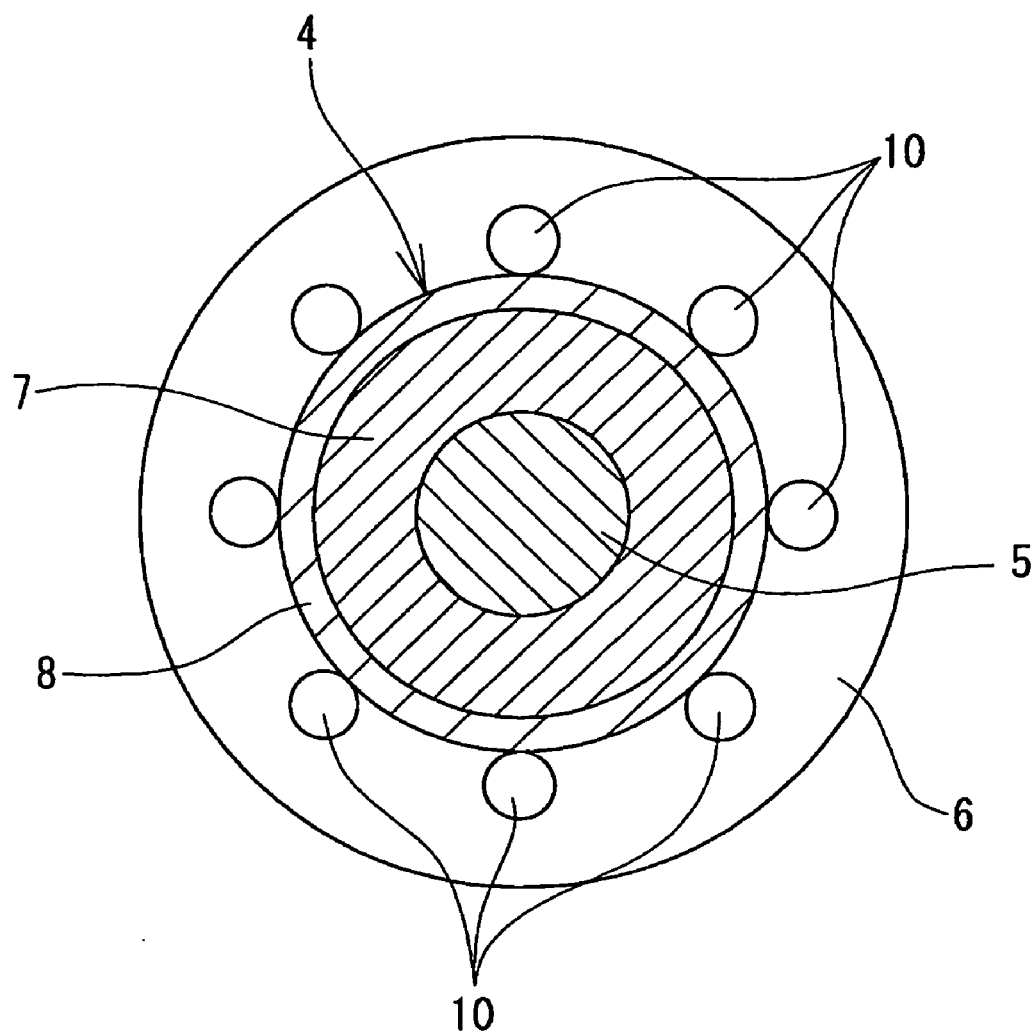
FIG. 2 is a sectional view taken along line II—II of FIG. 1.
Figure 3:
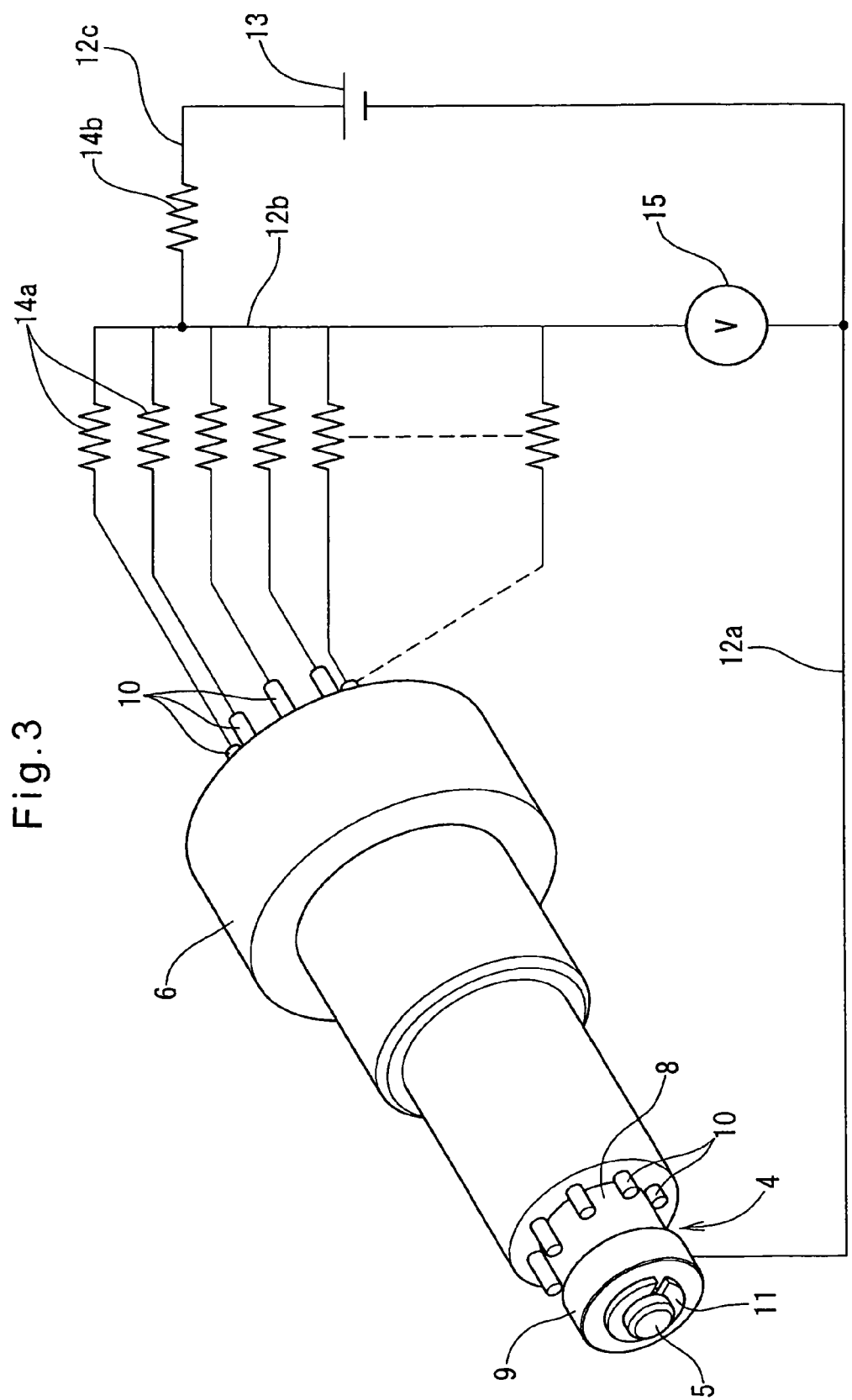
FIG. 3 schematically shows a sensor head assembly and a circuit of the sensor of FIG. 1.

As shown in FIG. 2, the eight conductors 10 are arranged around the rod 5 so as to be circumferentially equidistantly spaced from each other. As shown in FIG. 3, the conductors 10 have their tips positioned such that their axial distances from the rear end of the first electrode 9 increase in one circumferential direction so that they are all different from one another. The first electrode 9 is fastened to the rod 5 near its distal end by means of a snap ring 11 so as not to slip off of the rod 5.

As shown in FIGS. 1 and 3, the rod 5 has its proximal end connected to the positive terminal of a DC power supply 13 through a lead 12a. The conductors 10 have their respective proximal ends connected through fixed resistors 14a having identical resistivities Ra to a common lead 12b which is in turn connected to the negative terminal of the power supply 13 through a lead 12c including a fixed resistor 14b having a resistivity Rb. Between the lead 12b and the positive terminal of the power supply 13, a voltmeter 15 for detecting the partial voltage V of the sensor head assembly 4 is provided.

The oil condition sensor of the first embodiment detects the degree of contamination of oil as follows. In this embodiment, the supply voltage $V_0$ of the DC power supply 13 is 5 V and the resistivities Ra and Rb of the fixed resistors 14a and 14b are 1 kΩ and 600 Ω, respectively. While the oil is clean and metallic powder is scarcely stuck on the sensor head assembly 4, no short circuit occurs between the first electrode 9 and any of the conductors 10. Thus, the resistance R between the first and second electrodes will be infinite, so that the partial voltage V of the sensor head assembly 4, as detected by the voltmeter 15, will be equal to the supply voltage $V_0$, i.e. 5 V (see FIG. 4).

When the oil becomes increasingly contaminated, the conductors 10 will be electrically connected to the electrode 9 one after another with those closer to the electrode 9 earlier. When n (number) of the eight conductors 10 are electrically connected to the electrode 9, the resistance R between the first and second electrodes will be Ra/n. Thus, the partial voltage V of the sensor head assembly 4 is given by the following equation.

$$V = V_0 \cdot R/(R+Rb) \quad (1)$$

where R=Ra/n, $V_0$=5 V, Ra=1 kΩ, and Rb=600 Ω

Figure 4:
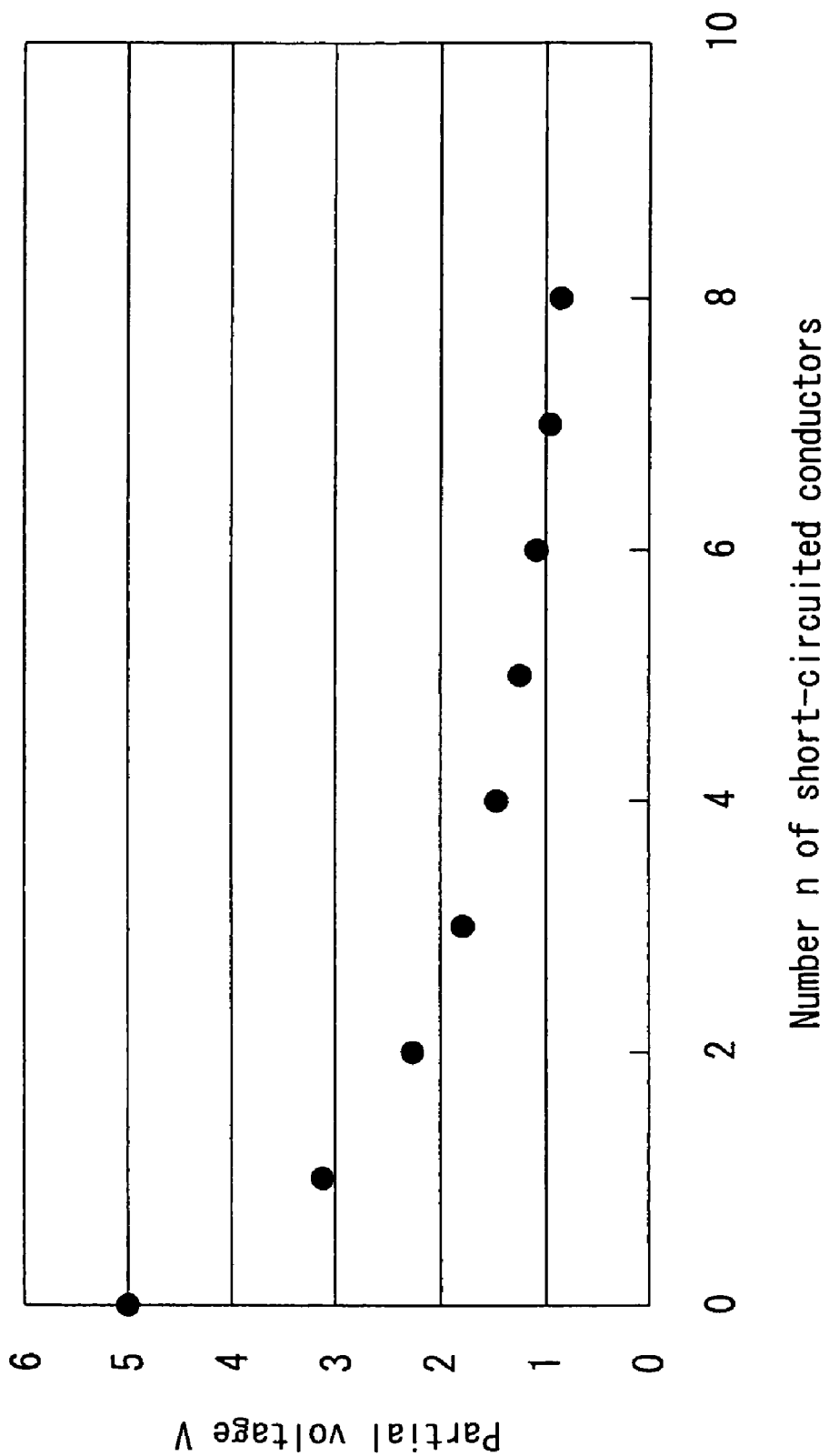
FIG. 4 is a graph showing the relationship between the number n of conductors that are electrically connected to the axially opposed electrode and the partial voltage V.

As is apparent from the above equation and the graph of FIG. 4, the smaller the partial voltage V detected by the voltmeter 15, the greater the number n of conductors 10 that are electrically connected to the electrode 9, and thus the higher the degree to which the oil is contaminated with metallic powder. Thus, by reading the voltmeter 15, the degree of contamination of the oil can be determined with high accuracy.

In the first embodiment, eight rod-shaped conductors are used, and the fixed resistors connected to the proximal ends of the conductors have resistivities equal to one another. But the number of rod-shaped conductors may be greater or smaller than eight. Also, the fixed resistors connected to the respective conductors may have different respective resistivities. For example, the resistivities of the fixed resistors may be determined such that the shorter the distance between the electrode 9 and any particular conductor 10, the greater the resistivity of the fixed resistor connected to this particular conductor 10 so that the partial voltage V decreases more uniformly with an increase in the number of conductors 10 that are electrically connected to the electrode 9.

Figure 5:
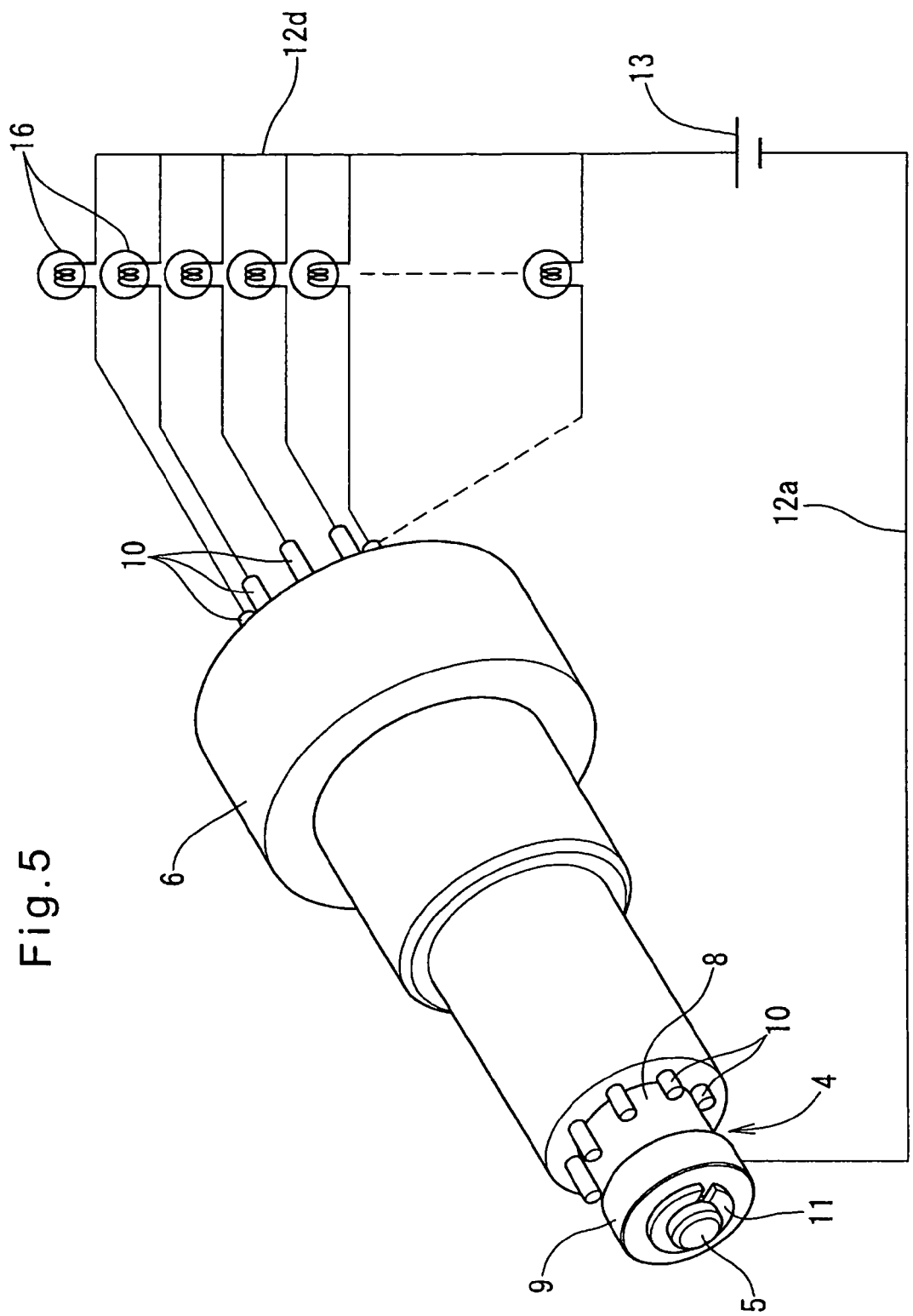
FIG. 5 schematically shows an oil condition sensor of a second embodiment, especially its sensor head assembly and a circuit therefor.

FIG. 5 shows the second embodiment, which differs from the first embodiment in that the fixed resistors 14a connected to the proximal ends of the respective conductors 10 are replaced with small light bulbs 16, and the light bulbs 16 are connected to the negative terminal of the DC power supply 13 through a lead 12d. In this embodiment, the number of conductors 10 that are electrically connected to the electrode 9 is determined by counting the number of bulbs 16 that are turned on.

In either embodiment, the permanent magnet 7 is used to magnetically attract metallic powder to the sensor head assembly 4. But instead of the permanent magnet 7, an electromagnet may be used. In either embodiment, only the second electrode comprises a plurality of conductors, i.e. conductors 10. But the first electrode 9 may also formed of a plurality of conductors.

What is claimed is:

1. An oil condition sensor comprising a rod having a tip portion adapted to be immersed in oil, a magnet mounted around said tip portion, a pair of electrodes mounted around said magnet so as to be axially spaced from each other, one of said pair of electrodes comprising a plurality of conductors, said conductors being electrically connectable to the other of said pair of electrodes through any metallic powder present in the oil, whereby the amount of metallic powder in the oil is inferable from the number of conductors that are electrically connected to the other of said pair of electrodes.

2. The oil condition sensor of claim 1 wherein said conductors are connected to a power supply through separate fixed resistors.

3. The oil condition sensor of claim 1 wherein said conductors are connected to a power supply through separate elements that react to electricity passed therethrough.

4. The oil condition sensor of claim 1 wherein each of said conductors is spaced from the other of said pair of electrodes by a distance that is different from any of the distances between the other of said conductors and the other of said pair of electrodes.

5. The oil condition sensor of claim 2 wherein each of said conductors is spaced from the other of said pair of electrodes by a distance that is different from any of the distances between the other of said conductors and the other of said pair of electrodes.

6. The oil condition sensor of claim 3 wherein each of said conductors is spaced from the other of said pair of electrodes by a distance that is different from any of the distances between the other of said conductors and the other of said pair of electrodes.

* * * * *